(12) United States Patent
Pudil et al.

(10) Patent No.: US 9,981,245 B2
(45) Date of Patent: May 29, 2018

(54) METHOD AND APPARATUS FOR ZIRCONIUM OXIDE RECHARGING

(71) Applicant: Medtronic, Inc., Minneapolis, MN (US)

(72) Inventors: Bryant J. Pudil, Plymouth, MN (US); Martin T. Gerber, Maple Grove, MN (US); Christopher M. Hobot, Tonka Bay, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 340 days.

(21) Appl. No.: 14/722,068

(22) Filed: May 26, 2015

(65) Prior Publication Data

US 2015/0251161 A1 Sep. 10, 2015

Related U.S. Application Data

(63) Continuation-in-part of application No. 14/261,651, filed on Apr. 25, 2014, and a continuation-in-part of application No. 14/642,847, filed on Mar. 10, 2015.
(Continued)

(51) Int. Cl.
*B01D 35/00* (2006.01)
*B01J 20/34* (2006.01)
(Continued)

(52) U.S. Cl.
CPC ........ *B01J 20/3475* (2013.01); *A61M 1/1696* (2013.01); *B01D 15/203* (2013.01); *B01J 20/06* (2013.01)

(58) Field of Classification Search
None
See application file for complete search history.

(56) References Cited

U.S. PATENT DOCUMENTS 3,850,835 A 11/1974 Marantz
4,192,748 A 3/1980 Hyden
(Continued)

FOREIGN PATENT DOCUMENTS

EP 2446908 A1 5/2012
JP 2981573 B2 11/1999
(Continued)

OTHER PUBLICATIONS

PCT/US2015/019901 International Search Report and Written Opinion dated Jun. 5, 2015.
(Continued)

*Primary Examiner* — Richard C Gurtowski
(74) *Attorney, Agent, or Firm* — Roger Hahn; Kenneth Collier

(57) ABSTRACT

Methods and related apparatuses for sorbent recharging are provided. The methods and related apparatuses for recharging can recharge a specific rechargeable layer of a sorbent material such as zirconium oxide and/or zirconium phosphate in a sorbent cartridge. The methods and apparatuses include passing solutions containing aqueous basic solutions through the zirconium oxide. The apparatus allows for recharging the zirconium oxide, and also for recharging zirconium phosphate, wherein the sorbent materials are contained in reusable sorbent modules.

27 Claims, 10 Drawing Sheets

Related U.S. Application Data

(60) Provisional application No. 61/941,672, filed on Feb. 19, 2014, provisional application No. 61/909,372, filed on Nov. 26, 2013, provisional application No. 62/016,613, filed on Jun. 24, 2014, provisional application No. 62/077,159, filed on Nov. 7, 2014.

(51) Int. Cl.
    *B01J 20/06*    (2006.01)
    *B01D 15/20*    (2006.01)
    *A61M 1/16*    (2006.01)

(56) References Cited

U.S. PATENT DOCUMENTS

| | | |
|---|---|---|
| 6,579,460 B1 | 6/2003 | Willis |
| 2002/0112609 A1 | 8/2002 | Wong |
| 2003/0097086 A1 | 5/2003 | Gura |
| 2005/0056592 A1 | 3/2005 | Braunger |
| 2006/0241543 A1 | 10/2006 | Gura |
| 2008/0011664 A1 | 1/2008 | Karoor |
| 2008/0241031 A1* | 10/2008 | Li ............... B01D 53/8609 423/213.2 |
| 2009/0101552 A1 | 4/2009 | Fulkerson |
| 2009/0282980 A1 | 11/2009 | Gura |
| 2010/0004588 A1 | 1/2010 | Yeh |
| 2010/0078387 A1 | 4/2010 | Wong |
| 2010/0312172 A1 | 12/2010 | Hoffman |
| 2011/0017665 A1 | 1/2011 | Updyke |
| 2011/0048949 A1 | 3/2011 | Ding et al. |
| 2011/0171713 A1 | 7/2011 | Bluchel |
| 2011/0272352 A1 | 11/2011 | Braig |
| 2012/0273354 A1 | 11/2012 | Orhan et al. |
| 2013/0199998 A1 | 8/2013 | Kelly |
| 2014/0158588 A1 | 6/2014 | Pudil |
| 2014/0158623 A1 | 6/2014 | Pudil |
| 2015/0108069 A1* | 4/2015 | Merchant ......... A61M 1/1696 210/681 |
| 2015/0251161 A1 | 9/2015 | Pudil |
| 2015/0251162 A1 | 9/2015 | Pudil |
| 2015/0367055 A1 | 12/2015 | Pudil |

FOREIGN PATENT DOCUMENTS

| | | |
|---|---|---|
| JP | 200744602 | 2/2007 |
| WO | WO 2011/017215 A1 | 2/2011 |
| WO | WO 2013/019994 | 2/2013 |
| WO | WO 2013019179 | 2/2013 |
| WO | 2013101888 | 7/2013 |
| WO | WO 2013/103607 A1 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

PCT/US2015/032492 International Search Report dated Nov. 19, 2015.
PCT/US2015/032492 Written Opinion dated Nov. 19, 2015.
Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/019901 Written Opinion dated May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 Written Opinion dated Jul. 27, 2016.
PCT/US2016/030319 International Search Report dated Jul. 27, 2016.
PCT/US2016/030320 International Search Report dated Jul. 28, 2016.
PCT/US2016/030320 Written Opinion dated Jul. 28, 2016.
PCT/US2015/032485 International Search Report and Written Opinion dated Oct. 16, 2015.
PCT/US2016/030320 International Preliminary Report on Patentability, dated Apr. 20, 2017.
PCT/US2015/032485 Written Opinion dated May 9, 2016.
PCT/US2015/032494 International Preliminary Report on Patentablity dated Dec. 27, 2016.
European Search Report and Supplemental Search Report in European Application No. 14865374.4 dated Jun. 12, 2017.
European Search Report for App. No. 15812081.6, dated Mar. 8, 2018.
European Search Report for Ep App. No. 15811326.6, dated Feb. 14, 2018.
European Search Report for EP 15812413.1 date of completion is Feb. 6, 2018 (7 pages).

\* cited by examiner

METHOD AND APPARATUS FOR ZIRCONIUM OXIDE RECHARGING

CROSS REFERENCE

The present invention is a continuation-in-part (CIP) application of U.S. patent application Ser. No. 14/642,847, filed Mar. 10, 2015, which claims priority to U.S. Provisional Application No. 62/077,159, filed Nov. 7, 2014, and U.S. Provisional Application No. 62/016,613, filed Jun. 24, 2014, the contents of each incorporated herein in their entirety by reference. The present invention is also a continuation-in-part (CIP) application of U.S. patent application Ser. No. 14/261,651, filed Apr. 25, 2014, which claims priority to U.S. Provisional Application No. 61/909,372, filed Nov. 26, 2013, and U.S. Provisional Application No. 61/941,672, filed Feb. 19, 2014, the contents of each incorporated herein in their entirety by reference.

FIELD OF THE INVENTION

The invention relates to a method and related apparatus for sorbent material recharging, in particular, zirconium oxide. The method and related apparatus for recharging can recharge a specific rechargeable layer or module of a sorbent material containing zirconium oxide. The method and apparatus can also be adapted to recharge both zirconium oxide and zirconium phosphate. A solution or solutions containing appropriate solutes can be passed through the sorbent materials to recharge the materials. Zirconium oxide and zirconium phosphate may be included in a sorbent cartridge or module, and the zirconium oxide and zirconium phosphate may be recharged without removing the sorbent materials from the sorbent cartridge or module.

BACKGROUND

Zirconium oxide is a common material used in sorbent cartridges for sorbent dialysis. Zirconium oxide can remove phosphate ions, fluoride ions and other anions from spent dialysate, exchanging these ions for acetate or hydroxide anions. Known sorbent dialysis systems do not provide for a way to recharge the zirconium oxide present in a sorbent cartridge so the zirconium oxide can be reused for future dialysis sessions. Instead, known sorbent dialysis systems generally require the sorbent materials to be discarded and the sorbent cartridge replaced after each use. Although traditional sorbent cartridges can be broken down to extract the sorbent materials for recharging, the sorbent materials must be re-processed at a processing plant, and cannot be recharged by the dialysis machine, a recharging device, or an in-clinic apparatus. The exhausted sorbent materials must be transported to a processing plant, the sorbent cartridge disassembled and the sorbent materials recharged by the plant. At some point, a new cartridge must be manufactured and the recharged sorbent materials re-packaged into the cartridge and transported back to the dialysis clinic for use. Traditional cartridges also cannot isolate specific materials into compartments for recharging, and therefore, cannot be adapted to recharge expensive rechargeable sorbent materials such as zirconium oxide or zirconium phosphate, and dispose of less expensive materials such as urease, alumina, and/or activated carbon. Single- and limited-use sorbent cartridges drive up not only the unit cost of dialysis, but also the total cost of dialysis.

There is a need for systems and methods for recharging sorbent materials such as zirconium oxide for reuse. There is also a need for methods and systems for separating sorbent materials within a sorbent cartridge into single and multi-use modules that can facilitate recharging and reuse of at least one of the sorbent materials. There is a further need for systems and related methods whereby rechargeable sorbent materials can be separated into multi-use modules and single-use modules wherein non-rechargeable sorbent materials can optionally be in one or more separate modules. There is also a need for an apparatus that can facilitate recharging of multiple sorbent materials in separate modules, such as zirconium oxide and zirconium phosphate.

SUMMARY OF THE INVENTION

The first aspect of the invention relates to a method of recharging zirconium oxide. In any embodiment of the first aspect of the invention, the method can comprise the steps of recharging zirconium oxide by passing a basic aqueous solution through the zirconium oxide; wherein the zirconium oxide is present in a multi-use sorbent module for sorbent dialysis.

In any embodiment of the first aspect of the invention, the multi-use sorbent module can be connectable to one or more additional sorbent modules containing sorbent materials to form a sorbent cartridge.

In any embodiment of the first aspect of the invention, the basic aqueous solution can comprise any one or more bases selected from the group consisting of s sodium hydroxide, lithium hydroxide, potassium hydroxide, and combinations thereof.

In any embodiment of the first aspect of the invention, the concentration of the base can be between any of 0.1 M and 5.0 M, 0.1 M and 0.5 M, 0.3 M and 0.7 M, 0.6 M and 1.0 M, 0.5 M and 1.5 M, 1.0 M and 2.5 M, 2.0 M and 3.5 M, or 3.0 M and 5.0 M.

In any embodiment of the first aspect of the invention, the method can comprise maintaining a temperature of the basic aqueous solution at between any of about 20° C. and about 105° C., 25° C. to about 80° C., 35° C. to about 75° C., 40° C. to about 70° C., 50° C. to about 60° C., 25° C. to about 50° C., 50° C. to about 75° C., or 60° C. to about 105° C.

In any embodiment of the first aspect of the invention, the flow rate of the basic aqueous solution passed through the zirconium oxide can be between any of 10 ml/min to 750 ml/min, 10 ml/min to 100 ml/min, 50 ml/min to 250 ml/min, 200 ml/min to 250 ml/min, 250 ml/min to 400 ml/min, 300 ml/min to 550 ml/min and 500 ml/min to 750 ml/min.

In any embodiment of the first aspect of the invention, the method can comprise rinsing the zirconium oxide with water after passing the basic aqueous solution through the zirconium oxide.

In any embodiment of the first aspect of the invention, the method can comprise draining the zirconium oxide after rinsing the zirconium oxide by blowing air through the zirconium oxide.

In any embodiment of the first aspect of the invention, the recharging process can be carried out by a recharger.

The features disclosed as being part of the first aspect of the invention can be in the first aspect of the invention, either alone or in combination.

The second aspect of the invention is related to a recharger. In any embodiment of the second aspect of the invention, the recharger can comprise a first fluid source fluidly connectable to at least a first multi-use sorbent module for sorbent dialysis; wherein the first multi-use module is configured to contain zirconium oxide; wherein the first fluid source is configured to contain a first recharging solution capable of recharging the zirconium oxide in the first multi-use module; and a fluid flow path fluidly connecting the first fluid source and an inlet of the first multi-use sorbent module.

In any embodiment of the second aspect of the invention, fluid flow through the fluid flow path can be controlled by a pump.

In any embodiment of the second aspect of the invention, the first recharging solution can be a basic aqueous solution.

In any embodiment of the second aspect of the invention, the recharger can comprise fluid connections to at least a second multi-use module.

In any embodiment of the second aspect of the invention, the first and second multi-use modules can contain the same sorbent material.

In any embodiment of the second aspect of the invention, the fluid flow path can fluidly connect the first fluid source to each of the first and second multi-use modules.

In any embodiment of the second aspect of the invention, the first multi-use module can contain a sorbent material different from a sorbent material in the second multi-use module.

In any embodiment of the second aspect of the invention, the recharger can comprise a second fluid source configured to contain a second recharging solution different from the first recharging solution, a second fluid flow path fluidly connecting the second fluid source to the second multi-use module.

In any embodiment of the second aspect of the invention, the second multi-use module can contain zirconium phosphate and the second recharging solution can be a solution of an acid, a buffer, a sodium salt, or combinations thereof.

In any embodiment of the second aspect of the invention, wherein fluid flow through the first fluid flow path is controlled by a first pump; and wherein fluid flow through the second fluid flow path is controlled by a second pump.

In any embodiment of the second aspect of the invention, the recharger can comprise a water source, wherein the water source is fluidly connectable to the fluid flow path.

In any embodiment of the second aspect of the invention, the fluid flow path can comprise a valve, wherein the valve controls the movement of fluid from either the first fluid source or the water source into the fluid flow path.

In any embodiment of the second aspect of the invention, the recharger can comprise a heater in the fluid flow path; wherein the heater heats the first recharging fluid before the first recharging fluid enters the first multi-use module.

In any embodiment of the second aspect of the invention, the recharger can comprise a heat exchanger, wherein the heat exchanger comprises at least a first compartment and a second compartment, wherein fluid in the fluid flow path enters the first compartment before the heater heats the fluid and before entering the first multi-use module, and wherein the fluid flow path fluidly connects an outlet of the first multi-use module to the second compartment of the heat exchanger.

In any embodiment of the second aspect of the invention, the recharger can comprise a first heater and a second heater, wherein the first heater heats the first recharging solution before the first recharging solution enters the first multi-use module, and wherein the second heater heats the second recharging solution before the second recharging solution enters the second multi-use module.

In any embodiment of the second aspect of the invention, the recharger can comprise a heater, wherein the heater heats the first recharging solution before the first recharging solution enters the first multi-use module, and wherein the heater heats the second recharging solution before the second recharging solution enters the second multi-use module.

In any embodiment of the second aspect of the invention, the recharger can be fluidly connectable to at least two modules each configured to contain zirconium oxide.

In any embodiment of the second aspect of the invention, the recharger can be fluidly connectable to one or more modules configured to contain zirconium oxide and one or more modules configured to contain zirconium phosphate.

The features disclosed as being part of the second aspect of the invention can be in the second aspect of the invention, either alone or in combination.

DETAILED DESCRIPTION OF THE INVENTION

Figure 1:
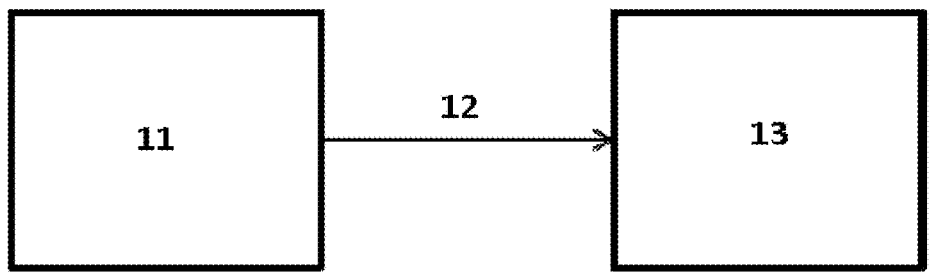
FIG. 1 shows a flow diagram illustrating a method of recharging zirconium oxide.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "acid" as used herein can be either a Lewis acid or a Brønsted-Lowry acid. A Lewis acid is a compound capable of accepting a lone pair of electrons. A Brønsted-Lowry acid is a compound capable of donating a hydrogen ion to another compound.

The term "anion exchanger" means a material that can bind a molecule having a negative charge and exchange another molecule having a charge for the bound molecule.

A "base" as used herein can be either a Lewis base or a Brønsted-Lowry base. A Lewis base is a compound capable of donating a lone pair of electrons. A Brønsted-Lowry base is a compound capable of accepting a hydrogen ion from another compound.

A "basic aqueous solution" is a solution of a base dissolved in water. The resulting basic aqueous solution will have a pH of above 7.

A "buffer solution" is a solution comprising a weak acid and the conjugate base of the weak acid or a weak base and the conjugate acid of the base.

The term "cartridge" refers to any container designed to contain a powder, fluid, or gas made for ready connection to a device, structure, system, flow path, or mechanism. The container can have one or more compartments. Instead of compartments, the container can also comprise a system of two or more modules connected together to form the cartridge wherein the two or more modules once formed can be connected to a device, structure, system, flow path, or mechanism.

The term "cation exchanger" means a material that can bind a molecule having a positive charge and exchange another molecule having a charge for the bound molecule.

"Clean" or "cleaning" refers to the process of removing impurities, toxins or biological material, such as by killing or rendering nonviable any bacteria, virus, fungus or other biologic material.

The term "comprising" includes, but is not limited to, whatever follows the word "comprising." Thus, use of the term indicates that the listed elements are required or mandatory but that other elements are optional and may or may not be present.

The term "configured to contain" means any particular form, alignment, shape, design, marking, or arrangement suitable for an intended material to be contained therein.

"Conjugate acid" refers to the compound formed after a base accepts a hydrogen ion from another compound.

"Conjugate base" refers to the compound formed after an acid donates a hydrogen ion to another compound.

The term "consisting of" includes and is limited to whatever follows the phrase "consisting of." Thus, the phrase indicates the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "contain" as used herein means to keep a material within a specific place. "Contain" can refer to materials placed within a component, absorbed onto a component, bound to a component, or any other method of keeping the material in a specific place.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. A "sorbent container" is any receptacle configured to hold one or more sorbent materials. Similarly, a "urease container" is any receptacle configured to hold urease.

The terms "detachable," "detached," or "detachably" relate to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane opposite to the fluid (e.g. blood) being dialyzed.

"Dialysate regeneration" refers to the process of treating spent dialysate, containing solutes removed from the patient's blood, with one or more sorbent materials to remove specific solutes, such as urea, and thereby generate dialysate that can be reused for dialysis.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis flow path" is the route in which a fluid will travel during dialysis.

A "dialysis session" refers to the medical procedure wherein dialysis is preformed on a patient.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Draining" refers to the process of removing a fluid from a component.

"Flow" refers to the movement of a fluid or a gas.

"Flow rate" refers to the amount of fluid that passes a particular point during a particular time period. A flow rate is commonly presented in milliliters of fluid per min, referring to the number of milliliters of fluid that will pass a particular point in one minute.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The term "fluidly connectable," "fluidly connect," and the like, refer to the ability of providing for the passage of fluid or gas from one point to another point. The two points can be within or between any one or more of compartments, modules, systems, components, and rechargers, all of any type. The connection can optionally be disconnected and then reconnected.

A "fluid source" is a source from which at least one fluid can be obtained. The fluid source can be a tank containing a fluid, a mixer into which multiple fluids can be added and mixed, a dedicated fluid line, such as a municipal water line, or any other source from which a fluid can be obtained.

"Functional capacity" is the ability of a material to accomplish the material's intended function. In some instances functional capacity can refer to the ability of a sorbent material to remove specific ions from a fluid, or to transform specific solutes into other materials.

A "heater" is a device capable of heating a fluid or gas.

A "heat exchanger" is a device comprising at least two compartments, wherein a fluid or gas can pass through one compartment, while a second fluid or gas can pass through the second compartment. The heat exchanger is configured to allow heat transfer between the two compartments such that if the fluids or gases in opposite compartments are at different temperatures, the higher temperature fluid or gas will act to heat up the lower temperature fluid or gas.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for dialysis. In such a case, the module can comprise one or more compartments within the module. Alternatively, two or more modules can form a cartridge to be fitted to a device or mechanism where each module individually carries separate components but only when connected together contain in summation all the necessary components for an intended purpose such as a sorbent for dialysis. A module can be referred to as a "first module," "second module," "third module," etc. to refer to any number of modules. The designation of "first," "second," "third," etc. does not refer to the respective placement of the module in the direction of fluid or gas flow, and merely distinguishes one module from another unless otherwise indicated.

A "multi-use module" is a module that can be used for more than one dialysis session, often with recharging of the sorbent materials inside the module between uses.

The term "passing a solution through" a component or material refers to the solution entering the component or material, moving through at least part of the component and material, and then exiting the component or material.

The terms "pathway," "conveyance pathway," "fluid flow path," and "flow path" refer to the route through which a fluid or a gas, such as dialysate or blood, travels, or the route a gas travels.

The term "pump" refers to any device that causes the movement of fluids or gases by applying suction or pressure.

A "recharger" is an apparatus designed to recharge at least one material.

"Recharging" refers to the process of treating a sorbent material to restore the functional capacity of the sorbent material so as to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a sorbent material such as urease. Notably, urease is not "recharged," but can be replenished, as defined herein.

A "recharging solution" is a solution comprising the appropriate ions for recharging a specific sorbent material.

"Replenishing" means to add back into a system, section or module, a material previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" or "reusing" refers in one instance to a solid, liquid, gas that can be used more than one time, optionally with treatment of any type of the material between uses. For example, a material and a solution can be reused. In one instance, reusable can refer to a cartridge, as used herein, that contains a material that can be recharged by recharging the material(s) within the cartridge.

"Rinsing" refers to passing a fluid, such as water, through a component to remove a fluid or solid previously in the component.

"Saturated" refers to a solution containing the maximum possible amount of a particular solute at a given temperature.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, and merely serves to distinguish one section from another unless otherwise indicated. Additionally, each section can be optionally physically separated such as by a divider or wall; however, referring to a particular section does not necessarily require physical separation and merely refer to a particular location in which a material is contained.

A "single-use module" is a module that contains sorbent materials not intended to be recharged. A "single-use" module can be used more than one time, but requires replenishing or refilling of the sorbent materials inside.

A "sodium salt" is an ionic compound made up of at least one sodium ion and at least one anion, wherein the ratio of sodium ions to anions is based on the charge of the anion, to achieve an electrically neutral compound.

A "solution," as used herein is a homogeneous mixture comprising a solvent and at least one solute, wherein the solute is dissolved in the solvent.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

A "sorbent cartridge module" or "sorbent module" means a discreet component of a sorbent cartridge. Multiple sorbent cartridge modules can be fitted together to form a sorbent cartridge of two or more sorbent cartridge modules. In some embodiments, a single sorbent cartridge module can contain all of the necessary materials for dialysis. In such cases, the sorbent cartridge module can be considered to be a "sorbent cartridge."

"Sorbent materials" are materials capable of removing specific solutes from solution, such as urea.

A "sorbent module" is a container containing at least one sorbent material. In some embodiments, the sorbent module can connect to another sorbent module to form a sorbent cartridge.

"Spent dialysate" is a dialysate contacted with blood through a dialysis membrane and contains one or more impurity, or waste species, or waste substance, such as urea.

A "valve" is a device capable of directing the flow of fluid or gas by opening, closing or obstructing one or more pathways to allow the fluid or gas to travel in a path. One or more valves configured to accomplish a desired flow can be configured into a "valve assembly."

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

A "water source" is a fluid source as defined herein, from which water can be obtained.

Zirconium Oxide Recharging

The first and second aspects of the invention provide for methods and related apparatuses for recharging a rechargeable sorbent material. The rechargeable sorbent material can be one or more and includes the group of zirconium phosphate, activated carbon, zirconium oxide, and rechargeable sorbent materials as defined herein. In particular, the first and second aspects of the invention provide for a method and apparatus for recharging zirconium oxide used in dialysis systems that can displace any phosphate, fluoride or other anions and replace them with acetate or hydroxide ions. By recharging the rechargeable sorbent material, and in particular, zirconium oxide, in this manner, the rechargeable sorbent material, such as zirconium oxide can be reused instead of discarded, reducing costs and waste. The rechargeable sorbent material such as zirconium oxide may be part of a sorbent dialysis system. In particular, zirconium oxide can be used to remove phosphate ions in spent dialysate that have passed through a dialysis membrane from the blood of a patient. By allowing the zirconium oxide and other sorbent materials to be recharged after use, the first and second aspects of the invention allow a sorbent cartridge or module containing the sorbent materials to also be reused more than once.

FIG. 1 shows a flow chart describing the process of recharging zirconium oxide. In any embodiment of the first or second aspects of the invention, the zirconium oxide can be present in a sorbent cartridge or sorbent module during the recharging process. Zirconium oxide 11 containing phosphate, fluoride and other anions removed from a dialysate can be treated by passing a fluid through the zirconium oxide containing a base in step 12. In any embodiment of the first or second aspects of the invention, the basic solution can be a sodium hydroxide solution. In any embodiment of the first or second aspects of the invention, the basic solution can use other bases, such as lithium hydroxide or potassium hydroxide. One skilled in the art will understand that other bases can be used in the recharging solution. The hydroxide ions present in the basic aqueous solution used in step 12 will displace the ions present on the zirconium oxide, creating a recharged zirconium oxide 13 containing hydroxide anions.

The recharged zirconium oxide 13 can then be used in sorbent dialysis, where anions present in spent dialysate will be exchanged by the zirconium oxide for hydroxide ions. In any embodiment of the first or second aspects of the invention, recharging can also include treating a sorbent material so as to clean the sorbent material so that the sorbent material can be stored and used in a subsequent dialysis session.

In any embodiment of the first or second aspects of the invention, the zirconium oxide recharging solution can have any concentration of base, including a saturated solution. In any embodiment of the first or second aspects of the invention, the zirconium oxide recharging solution can have a base concentration of between 0.1 and 5.0 M. One skilled in the art will understand that at lower concentrations of base, more recharging solution may be necessary to fully recharge the zirconium oxide, and a longer recharging time may be necessary. In any embodiment of the first or second aspects of the invention, the concentration of base in the recharging solution can be between any of 0.1 M and 5.0 M, 0.1 M and 0.5 M, 0.3 M and 0.7 M, 0.6 M and 1.0 M, 0.5 M and 1.5 M, 1.0 M and 2.5 M, 2.0 M and 3.5 M, or 3.0 M and 5.0 M.

In any embodiment of the first or second aspects of the invention, the recharging solution can be passed through the zirconium oxide at any rate. In any embodiment of the first or second aspects of the invention, the rate that the recharging solution can be passed through the zirconium oxide can be between 1 and 750 ml/min. One skilled in the art will understand that the faster the rate of the recharging solution being passed through the zirconium oxide, the more recharging solution that may be necessary. Additionally, although less recharging solution may be necessary at a slower flow rate, the recharging process may take a longer time to fully recharge the zirconium oxide. The rate that the recharging solution is passed through the zirconium oxide is therefore flexible and can be chosen by a user depending on the needs for a faster recharging time and use of less recharging materials. In any embodiment of the first or second aspects of the invention, the flow rate of the recharging solution can be between and of 1 ml/min to 750 ml/min, 10 ml/min to 100 ml/min, 50 ml/min to 250 ml/min, 200 ml/min to 250 ml/min, 250 ml/min to 400 ml/min, 300 ml/min to 550 ml/min and 500 ml/min to 750 ml/min.

In any embodiment of the first or second aspects of the invention, the temperature of the recharging solution can be controlled. In some cases increasing the temperature reduces the volume of recharge solution required to recharge the zirconium oxide. In some instances, increasing the temperature accelerates or makes possible cleaning of the zirconium oxide. In any embodiment of the first or second aspects of the invention, the temperature of the basic solution can be maintained in any range between about 20° C. to about 105° C., with the top temperature possible depending on the boiling point of the particular solution. For example, the ranges include 25° C. to about 80° C., 35° C. to about 75° C., 40° C. to about 70° C., 50° C. to about 60° C., 25° C. to about 50° C., 50° C. to about 75° C., or 60° C. to about 105° C.

Each of the variables of temperature, concentration and flow rate of the recharging solution can affect the amount of recharging solution necessary and the time necessary to recharge the zirconium oxide. Each of these variables can be controlled independently depending on the needs and capabilities of the system. For example, if there is a need to conserve the recharging solution, a slower flow rate can be used with a higher temperature. In any embodiment of the first or second aspects of the invention, a base solution such as NaOH ranging from 0.1 to 5.0M can be passed through a sorbent module containing zirconium oxide weighing in a range from 0.01 to 1.5 kg. The temperature can be controlled to between 1 and 100° C., and include ranges such as 20 to 80° C., 15 to 95° C., 25 to 95° C., 45 to 90° C., 20 to 60° C., 50 to 80° C., or 25 to 75° C. Additionally, the flow rate of the recharging solution can be any one of 1 to 2,000 ml/min, 10 to 1,550 ml/min, 10 to 1,250 ml/min, 10 to 950 ml/min, 10 to 850 ml/min, 10 to 750 ml/min, 10 to 650 ml/min, or 10 to 550 ml/min. The conductivity of the recharging fluid can range from any one of 5 to 100 mS/cm, 20 to 80 mS/cm, 25 to 75 mS/cm, 35 to 65 mS/cm, 10 to 40 mS/cm, 45 to 55 mS/cm, or 55 to 100 mS/cm where mS/cm (Siemens equal 1/ohms). The recharging time can range from 1-60, 2-45, 5-40, 10-60, 1-10, 1-30, 25-60, 15-30, or 10-30 minutes. The volume of recharging fluid can range from any one of 0.65 to 32.5 L, 1.55 to 30.5 L, 2.50 to 25.5 L, 3.5 to 30.5 L, 5.0 to 27.5 L, 6.5 to 32.5 L, or 6.5 to 12.5 L. In one embodiment, a 0.5 M solution of NaOH was passed through a sorbent module containing 0.33 kg of zirconium oxide. The recharging solution can be controlled to be between 20 and 80° C. with a flow rate of 217 ml/min. The zirconium oxide can be recharged after about 30 minutes of the recharging process, necessitating about 6.5 L of recharging solution. In another embodiment, a 0.65 M solution of NaOH can be passed through a sorbent module containing 0.35 kg of zirconium oxide. The recharging solution can be controlled to be between 30 and 90° C. with a flow rate of 317 ml/min. The zirconium oxide can be recharged after about 25 minutes of the recharging process, necessitating about 7.5 L of recharging solution. In yet another embodiment, a 0.55 M solution of NaOH can be passed through a sorbent module containing 0.41 kg of zirconium oxide. The recharging solution can be controlled to be between 40 and 100° C. with a flow rate of 417 ml/min. The zirconium oxide can be recharged after about 15 minutes of the recharging process, necessitating about 6.0 L of recharging solution. One skilled in the art will understand that the variables listed can be changed and still recharge the zirconium oxide with a different amount of recharging solution, as necessary.

One skilled in the art will understand that a lower temperature can be used with a longer recharging time. In certain environments, such as an at-home environment, it may be desirable to use a lower temperature and a longer recharging duration. A lower temperature can result in a lower demand on the heater, which can allow recharging with a lower system current drain. This may allow the recharger to be used with a standard wall outlet having a lower current. In any embodiment of the first or second aspects of the invention, a lower temperature can be used and the recharge time can be increased to at least 60 minutes or longer.

In any embodiment of the first or second aspects of the invention, the recharger can also have configurations that are specifically designed to fit into different sites of service, such has home, mobile, dedicated sorbent based dialysis clinics, in the first, second, and third aspects of the present invention. Rechargers that have the ability to recharge multiple multi-use modules and can accommodate different service sites are contemplated by this invention.

In any embodiment of the first or second aspects of the invention, a recharging process is not limited to a particular time of duration, and can be shortened or expanded based on a user's need or service sites, such as home, mobile stations, or dialysis centers. When the duration time is changed, other recharging conditions may also be changed, such as recharging temperatures.

At home dialysis refers to dialysis carried out by a user in his or her residence or other building outside of a clinical setting. At home dialysis may occur under hospice care or other medical supervision of doctors, nurses, or clinicians, but these are not always necessary. In order to facilitate recharging and reuse of sorbent materials in an at-home setting, the systems and methods are easily adaptable for use with the infrastructure common in homes having plumbing and electricity. However, at-home encompasses many other types of homes or out-of-clinic settings including homes and settings in less developed areas. The systems and methods can be used in those areas, countries, or locales where support infrastructure is minimal by relying on portable power generators and water reservoir tanks.

A mobile setting for dialysis refers to a movable dialysis setting. A mobile setting may comprise a mobile dialysis unit dispatched to one or more locations to provide dialysis to patients. The dialysis unit may be a large unit, capable of providing dialysis for multiple patients in a central location, or may be a smaller unit, capable of providing dialysis for only one or a few patients in a particular location. Often, a mobile dialysis unit may have little permanent infrastructure or support. The mobile dialysis unit may arrive at a location and set up a "pop-up" dialysis clinic, or a dialysis clinic that is only in a particular location for a brief time.

A dialysis center or clinic refers to a permanent location providing dialysis to patients. The dialysis center or dialysis clinic may employ doctors, nurses, or dialysis technicians to provide dialysis for multiple patients simultaneously. The dialysis clinics can be any size, ranging from clinics designed for one or two patients to clinics designed for dozens of patients or more.

A recharger system and method capable of working at a home, in a mobile setting or in a dialysis center allows for reuse of sorbent materials in these settings without the need to send the sorbent material to a recharging facility. Further, a recharger capable of operating without expensive and extensive infrastructure and support can facilitate use in these settings. As described, the recharger and methods can be configured to allow easy use in non-traditional dialysis settings, facilitating home, mobile or clinic dialysis. In any embodiment of the first or second aspects of the invention, a user can use a sorbent cartridge in a dialysis session at one time of the day, and slowly recharge the sorbent cartridge or modules throughout the rest of the day, or portion of the day. For example, a user may undergo sorbent dialysis at night, and the sorbent modules can be recharged throughout the following day. This allows for a lower temperature recharging, and/or lower concentrations of recharging solutions, making the recharging solutions easier for users of varying skill. To facilitate the ability of mobile dialysis centers to provide treatment and then move on to a new location, a recharger as described requiring less infrastructure and that is easily used is important. In any embodiment of the first or second aspects of the invention, the recharging can be carried out in a dialysis center, or a clinic designed to carry out dialysis on multiple patients, under the control of doctors or technicians.

One skilled in the art will understand that less recharging solution can be used, or the recharging process can be sped up, if fully recharging the zirconium oxide is unnecessary. For example, if only 75% of the original zirconium oxide functional capacity is needed for a new dialysis session, the recharging process can be halted after only 75% of the zirconium oxide is recharged.

Figure 2:
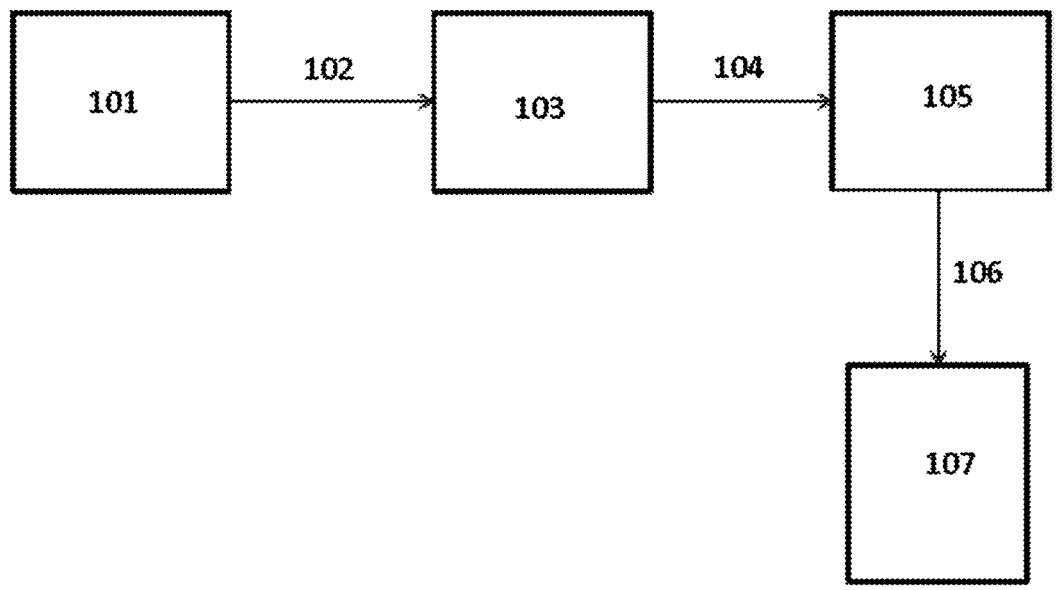
FIG. 2 shows a flow diagram illustrating a method of recharging zirconium oxide, including rinsing and draining of the zirconium oxide.

FIG. 2 shows a flow chart illustrating a full recharging process. Zirconium oxide 101, containing phosphate and other anions can be treated with a recharging solution in step 102. The recharging solution used in step 102 can be the same as the recharging solutions described regarding FIG. 1. The result will be recharged zirconium oxide 103. The recharged zirconium oxide 103 can then be rinsed with water to remove the recharging solution and any residual material in step 104 to create a rinsed zirconium oxide 105. The rinse water can be passed through the zirconium oxide in step 104 at any rate. One skilled in the art will understand that the higher the flow rate of the rinse water solution, the shorter the time period that will be necessary for fully rinsing the zirconium oxide. At the same time, at a higher rate a larger amount of water may be necessary for fully rinsing the zirconium oxide. In any embodiment of the first or second aspects of the invention, the flow rate of the water solution used in step 104 can be between 10 and 750 ml/min for a total volume of rinse water ranging from 0.25 to 2.0 L. The temperature of the water used to rinse the zirconium oxide in step 104 can also be controlled. In any embodiment of the first or second aspects of the invention, the temperature can be controlled to between 1 and 100° C. In any embodiment of the first or second aspects of the invention, the temperature of the water can be controlled to be less than about 45° C. Additionally, the flow rate of the water can be any one of 25 and 750 ml/min, 100 and 550 ml/min, 175 and 275 ml/min, 200 and 350 ml/min, 250 and 450 ml/min, 300 and 700 ml/min, 200 and 400 ml/min, or 350 and 750 ml/min. Other ranges are contemplated by the invention and can be used without departing from the scope of the invention. For example, in any embodiment of the first or second aspects of the invention, the flow rate of the rinse water through the zirconium oxide can be about 200, 300, 400, 500, 600, 700, 800, 900, or 1000 ml/min. The rinse time can range from 1-20, 2-18, 2-5, 2-6, 1-3, 2-3, 4-5, 4-6, or 3-6 minutes without departing from the scope of the invention. In specific embodiments, the flow rate can be 2.0 L of water at 100 ml/min at 29° C., for 10 minutes; 1.75 L of water at 150 ml/min at 28° C., for 8 minutes; 1.50 L of water at 175 ml/min at 27° C., for 7 minutes; 1.0 L of water at 200 ml/min at 25° C., for 5 minutes; or 0.75 L of water at 400 ml/min at 25° C., for 2 minutes. In any embodiment of the first or second aspects of the invention, the temperature can be lowered down to about 4° C. In any embodiment of the first or second aspects of the invention, the rinsing step 104 can also serve to cool down the zirconium oxide module where a high temperature was used in the recharging step 102. In any embodiment of the first or second aspects of the invention, the rinsing step 102 can be carried out with a fluid other than water. For example, bleach or other cleaning solution can be used that is capable of cleaning the module. In any embodiment of the first or second aspects of the invention, a cleaning solution can be passed through the module first, and then the module can be rinsed with water.

The water remaining in the rinsed zirconium oxide 105 can be removed by draining in step 106. To aid the draining process, air or another gas can be blown or drawn through the zirconium oxide to drive out the remaining water. In any embodiment of the first or second aspects of the invention, air or another gas can be pulled through the zirconium oxide using a pump or another means to create negative pressure at the outlet of the zirconium oxide container. In any embodiment of the first or second aspects of the invention, a combination of positive pressure at the zirconium oxide container inlet and negative pressure at the zirconium oxide outlet may also be used. In any embodiment of the first or second aspects of the invention, air can be blown through the zirconium oxide at any rate. In any embodiment of the first or second aspects of the invention, the flow rate of the air blown through the zirconium oxide can be between 100 and 1000 ml/min. In any embodiment, the flow rate of the air can be any one of 200 and 800 ml/min, 300 and 900 ml/min, 250 and 750 ml/min, 500 and 950 ml/min, 350 and 600 ml/min, 400 and 700 ml/min, 200 and 400 ml/min, or 300 and 800 ml/min. Other ranges are contemplated by the invention and can be used without departing from the scope of the invention. For example, in any embodiment of the first or second aspects of the invention, the flow rate of the air blown through the zirconium oxide can be about 200, 300, 400, 500, 600, 700, 800, 900, or 1000 ml/min. When using a pump to draw air through the module by positive pressure, the pump can be capable of drawing air through the module at any rate, including between any of 200 and 800 ml/min, 300 and 900 ml/min, 250 and 750 ml/min, 500 and 950 ml/min, 350 and 600 ml/min, 400 and 700 ml/min, 200 and 400 ml/min, or 300 and 800 ml/min. The blowing time can range from 1-20, 2-18, 2-5, 2-6, 1-3, 2-3, 4-5, 4-6, or 3-6 minutes without departing from the scope of the invention. In specific embodiments, the flow rate can be 400 ml/min at 27° C., for 3 minutes; the flow rate can be 500 ml/min at 26° C., for 2 minutes; the flow rate can be 600 ml/min at 25° C., for 2 minutes; the flow rate can be 700 ml/min at 24° C., for 2 minutes; the flow rate can be 800 ml/min at 25° C., for 1 minutes; the flow rate can be 600 ml/min at 24° C., for 5 minutes; or the flow rate can be 600 ml/min at 23° C., for 7 minutes. In any embodiment of the first or second aspects of the invention, the draining can be carried out at any ambient air temperature, including any temperature between about 4° C. to about 40° C. The result of the draining process is a recharged and drained zirconium oxide 107. The recharged and drained zirconium oxide 107 can then be stored until needed for a subsequent dialysis session. In any embodiment of the first or second aspects of the invention, the zirconium oxide 107 can be stored for any length of time, including between 1 min and 7 days, between 1 hour and 1 day, between 1 hour and 7 days, between 1 day and 7 days, between 1 day and 14 days, or between 7 days and 14 days. In any embodiment of the first or second aspects of the invention, the zirconium oxide 107 can be stored for any length of time, including more than 7 days.

As explained, in any embodiment of the first or second aspects of the invention, the zirconium oxide can be recharged within a sorbent module. Recharging the zirconium oxide within a sorbent module allows for the zirconium oxide to be recharged and reused easily, eliminating the need for refilling the zirconium oxide module before each use. However, in any embodiment of the first or second aspects of the invention, the zirconium oxide can be removed from the sorbent module and recharged separately. The recharged zirconium oxide can then be added back into the same or different sorbent module before using the zirconium oxide in dialysis.

Figure 3:
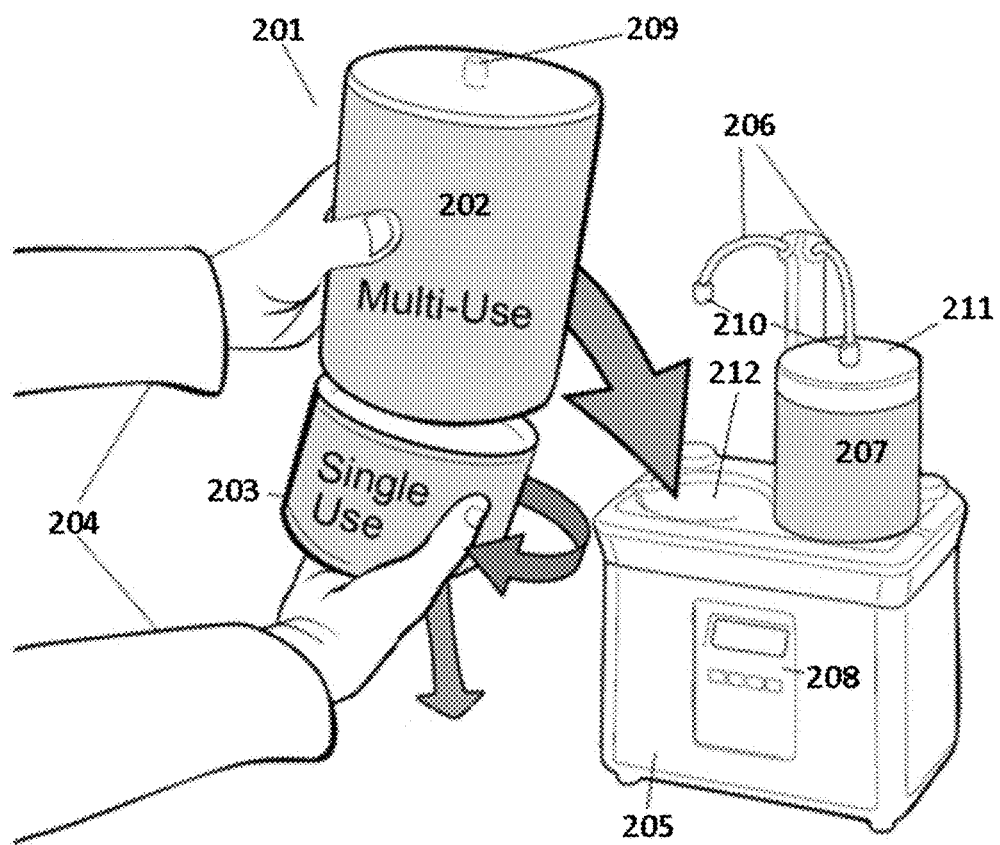
FIG. 3 shows a recharger configured to recharge two multi-use sorbent modules.

FIG. 3 shows an embodiment of a process of recharging a sorbent module of the first and second aspects of the invention, having a rechargeable sorbent material, specifically, zirconium oxide. As shown in FIG. 3, the sorbent cartridge 201 can be a modular dialysate regeneration assembly. In general, a modular dialysate regeneration assembly can be one or more sorbent compartments containing at least one sorbent material attached to at least another sorbent compartment. That is, the sorbent cartridge 201 can comprise multiple modules. Each module can be detachably connected to the other module or modules. The modules, when attached can form a fluid connection as described to allow fluid to flow from one module into another. The modules can be detached as shown in FIG. 3 into separate components to facilitate the recharging of rechargeable sorbent materials. The sorbent cartridge 201 may contain a multi-use module 202 which contains zirconium oxide, and a single-use module 203 which comprises other sorbent materials, such as activated carbon, alumina, silica, urease, zirconium phosphate and ion-exchange resin. Single use module 203 can also contain zirconium oxide not intended to be recharged. In any embodiment of the first or second aspects of the invention, the sorbent cartridge 201 can be a single structure, with all sorbent materials in the same module. After use, the functional capacity of the modules may be reduced due to the binding of solutes from spent dialysate to the sorbent materials within the sorbent cartridge. The user 204 can disconnect the single-use module 203 from the multi-use module 202. The single use module can be discarded or sent to a recharging or replenishing facility for recharging or replenishing. The multi-use module 202 can be recharged to restore the functional capacity of the sorbent materials as described. The multi-use module 202 can also be replenished by adding back sorbent materials into the multi-use module 202. Sorbent systems with multiple modules are described in detail in U.S. application Ser. No. 14/261,651, filed on Apr. 25, 2014, and the contents thereof incorporated herein by their entirety. One skilled in the art will understand that sorbent cartridges comprising more than two modules are possible. Sorbent cartridges with three or more modules are contemplated by any embodiment of the first or second aspects of the invention.

In any embodiment of the first or second aspects of the invention, the reusable or multi-use module can be configured to contain a rechargeable sorbent material, such as zirconium oxide. The module can be of a size and shape suitable to hold an amount of zirconium oxide necessary for a dialysis session. In any embodiment of the first or second aspects of the invention, the module can be labeled or color coded to indicate the module is configured for containing zirconium oxide. In any embodiment of the first or second aspects of the invention, the module can include an RFID or barcode that, when scanned by a user, informs the user of the particular sorbent material that the reusable module is configured to contain.

As shown in FIG. 3, a recharging apparatus 205 can comprise a sorbent cartridge fluid inlet 206 and a sorbent cartridge fluid outlet (not shown), as shown by recharging sorbent module 207. The fluid inlet 206 can connect to the modules by attaching recharger connector 210 to sorbent module connector 209 (only shown for module 202). The proper solutions as described herein can pass through the multi-use modules as needed, such as with multi-use module 207 located on the recharging apparatus 205. Interface 208 can notify the user of the progress of the recharging process, or can be used by the user to select the proper solutions, concentrations, amounts, temperature or other variables described herein for the recharging process. In any embodiment of the first or second aspects of the invention, instead of the recharge connector 210 attaching directly to connector 209 on the multi use module 202, a separate connector 211 can be fitted to the multi use module, as shown with multi use module 207. This connector 211 can fit over the top of the multi use module 207 and facilitate the introduction of recharging solution into the multi-use module 207.

In any embodiment of the first or second aspects of the invention, the recharging solution can be recirculated. Solution that enters through the top connector 210 of the multi-use module 207 can exit the multi-use module 207 through the bottom and enter the basin of the recharging apparatus 205. The solution, in any embodiment of the first or second aspects of the invention, can then be passed back to the fluid inlet 206 and back into the multi-use module 207. A pump (not shown) in the base of the recharging apparatus 205 can pump the solution back to fluid inlet 206 for re-entry into multi-use module 207, forming a fluid flow loop. In any embodiment of the first or second aspects of the invention, the solution can be treated before the solution is passed back into the multi use module 207 as explained herein.

In any embodiment of the first or second aspects of the invention, the recharger 205 can accommodate multiple multi-use sorbent modules at the same time, such as both multi use sorbent modules 202 and 207 as shown in FIG. 3. Multi-use sorbent module 202 can be placed in space 212 while the recharging apparatus 205 is recharging multi use module 207. One skilled in the art will understand the invention is not limited to recharging systems that can accommodate two multi-use modules at the same time. Systems that can only accommodate a single multi-use module, as well as systems that can accommodate 3, 4, 5, or more multi-use modules simultaneously are contemplated by this invention. In any embodiment of the first or second aspects of the invention, the recharger can be constructed to recharge more modules than 2 modules at a time. For example, a bank of modules containing any combination of zirconium phosphate and/or zirconium oxide modules can be recharged with fluid connections, tanks, and appropriate fluid lines constructed for such multiple charging. The number of modules being charged at any one time can include a range from 3 to 6, 4 to 8, 5 to 10, 6 to 12, 7 to 14 or more. The total number of modules in the bank can be any number 2 or greater. For example, a bank may contain 3, 4, 5, 6, 7, 8, 9, 10, 11, 12, 13, or more multi-use modules. In any embodiment of the first or second aspects of the invention, the recharger can set the flow rates, temperatures and concentrations of the recharging solutions independently for each module or group of modules. A recharger that can accommodate a single multi-use module may be a preferred recharger for use in a home or other environments. Multiple module rechargers may be preferred in different environments. In any embodiment of the first or second aspects of the invention, the multiple modules that can be recharged with a single recharging apparatus can contain the same or different sorbent materials. For example, both modules can contain zirconium oxide, and both modules can be recharged with the same recharging fluid. In any embodiment of the first or second aspects of the invention, different multi-use modules can be recharged with the same apparatus, such as one multi-use module containing zirconium oxide that can be recharged with a basic aqueous solution, and a second multi-use module containing zirconium phosphate that can be recharged with acid or buffer and sodium salts.

The multi-use modules can connect to the recharger by any means known in the art. In any embodiment of the first or second aspects of the invention, the connection can be a screw type connection, wherein the multi-use module 202 can be placed in space 212 of FIG. 3 and twisted to lock the multi-use module 202 into the recharging apparatus 205. In any embodiment of the first or second aspects of the invention, the space 212 on the recharging apparatus 205 may be nearly the same circumference as the multi-use module 202. When the multi-use module 202 is placed into the space 212, the multi-use module 202 contacts the edges of space 212 and a seal can be formed between the edges of the space 212 and the multi-use module 202. In any embodiment of the first or second aspects of the invention, an o-ring, gasket or other sealing means can be used to ensure there is no fluid leakage. Other fluid connections are described.

In any embodiment of the first or second aspects of the invention, the recharging solution can be passed through the multi-use modules in the opposite direction that spent dialysate travels through the modules during dialysis. Passing the recharging solution through in the opposite direction may result in a more efficient recharging process. In any embodiment of the first or second aspects of the invention, the recharging solution can be passed through the module in the same direction as spent dialysate during a dialysis session.

Figure 4:
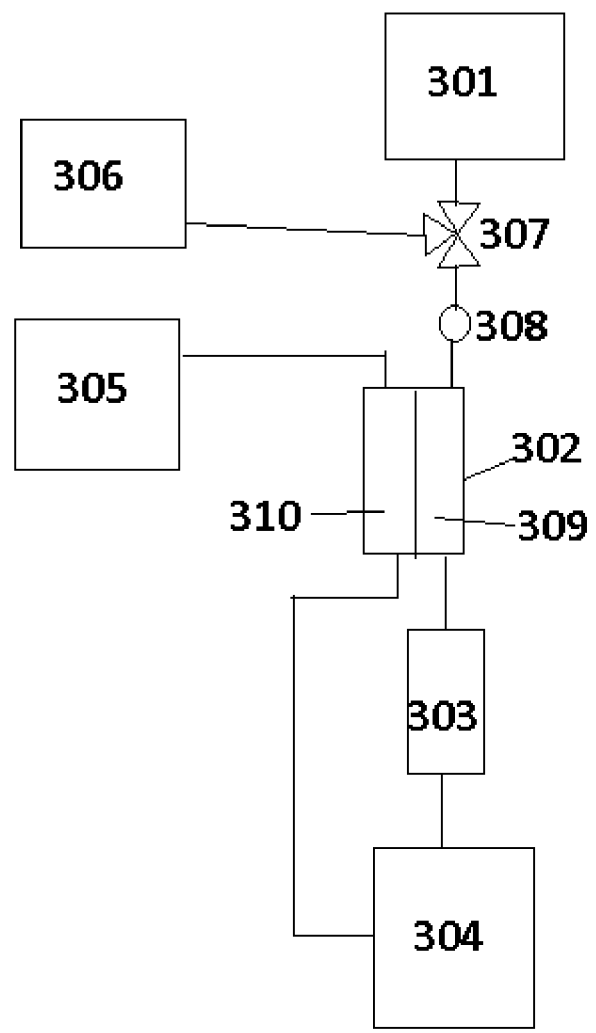
FIG. 4 shows a flow diagram of a recharger configured to recharge zirconium oxide.

FIG. 4 shows a flow diagram for use with a recharger in recharging zirconium oxide. Solution tank 301 can serve as a fluid source for a recharging solution. The recharging solution, as explained, can be placed in solution tank 301. The solution tank 301 can be fluidly connected to a heat exchanger 302, a heater 303 and a module containing zirconium oxide to be recharged 304. The recharging solution can pass through valve 307, the heat exchanger 302 and the heater 303 in order to be heated to the desired temperature as explained. Pump 308 can provide the driving force necessary to move the recharging solution through the zirconium oxide module 304 at the desired flow rate, as explained. The recharging solution, heated by heater 303 can pass through the zirconium oxide module 304 and then back through the heat exchanger 302. The heat exchanger 302 can be separated into two compartments; compartment 309 can contain a flow path for fresh recharging solution, while compartment 310 can contain a flow path for used recharging solution after passing through the zirconium oxide module 304. The solution in compartment 310 can still be at a higher temperature. As such, the solution in compartment 310 can act to heat the solution in compartment 309, reducing the requirements on the heater 303. In any embodiment of the first or second aspects of the invention, the heat exchanger 302 can be eliminated, and only heater 303 can control the temperature of the recharging solution entering zirconium oxide module 304. After passing through heat exchanger 302, the used solution can be diverted to a drain or storage container 305. In any embodiment of the first or second aspects of the invention, the fluid in storage container 305 can be neutralized and then disposed of.

As explained, after recharging the zirconium oxide in zirconium oxide module 304, the zirconium oxide can be rinsed with water or another fluid to remove any remaining recharging solution and to cool the zirconium oxide. Water or another liquid can be obtained from water reservoir 306, or from a dedicated water feed. Valve 307 can control whether fluid is being passed through the zirconium oxide module 304 from either recharging solution 301 or water reservoir 306.

As explained, in any embodiment of the first or second aspects of the invention, some or all of the recharging solution can be re-used by recirculating the recharging solution through the zirconium oxide module 304. This can be accomplished by connecting a fluid line from compartment 310 of the heat exchanger 302 back into recharging solution tank 301.

As explained, a single recharger can be used to recharge sorbent modules containing different sorbent materials, such as a sorbent module containing zirconium oxide and a sorbent module containing zirconium phosphate. Zirconium phosphate operates in a sorbent cartridge by removing calcium, potassium, magnesium and ammonium, along with other cations, from spent dialysate and replacing these ions with sodium and hydrogen ions. The ammonium ions are produced from the breakdown of urea by urease in the sorbent cartridge. To recharge zirconium phosphate, a recharging solution containing acid or buffer and sodium salts can be used. In any embodiment of the first or second aspects of the invention, the buffer used to recharge the zirconium phosphate can be acetic acid and sodium acetate, glycolic/glycolate solution, citric/citrate solution, propionate/propionic solution, monobasic phosphate, or any combination thereof. The hydrogen and sodium ions present in the recharging solution displace the potassium, calcium, magnesium and ammonium ions on the zirconium phosphate, resulting in a recharged zirconium phosphate. In any embodiment of the first or second aspects of the invention, the zirconium phosphate recharging solution can comprise between 0 M and saturated acetic acid, between 0 M and saturated sodium acetate and between 0 M and saturated sodium chloride. For example, the recharging solution can be between 0 M and saturated of any of the components. In any embodiment of the invention, the sodium salt can have a concentration of between any of 0.05 M to saturated, 0.05 M to 1.5 M, 1 M to 2.0 M, 1.8 M to 3.5 M, and 3.0 M to 5.0 M. In any embodiment of the first or second aspects of the invention, the acid concentration can be between any of 1 mM to 5000 mM, 15 mM to 500 mM, 100 mM to 2500 mM, 250 mM to 4000 mM, and 500 mM to 5000 mM. In any embodiment of the first or second aspects of the invention, the concentration of base used in the recharging solution can be between any of 0.01 M to saturated, 0.01 M to 0.2 M, 0.1 M to 0.3 M, 0.2 M to 1 M, and 0.8 M to 5.0 M. In any embodiment of the first or second aspects of the invention, the ranges can set based on a desired ratio of hydrogen and sodium ions bound to the zirconium phosphate after recharging. In any embodiment of the first or second aspects of the invention, the temperature of the zirconium phosphate recharging solution can be set to any temperature between 0 and 100° C., with the upper limit being dependent upon the boiling point of the particular solution used. In any embodiment of the first or second aspects of the invention, these ranges can be changed. In any embodiment of the first or second aspects of the invention, the pH of the buffer solution for recharging the zirconium phosphate can be between any of about 2 and about 8, about 3 and about 5, about 3.5 and about 4.8, or about 4.0 and about 4.5. The resulting sodium to hydrogen ratio on the recharged zirconium phosphate can depend on the relative concentrations of these ions in the recharging solution, and is therefore controllable. Further, other combinations than acetic acid, sodium acetate and sodium chloride can be used. One skilled in the art will understand that other acids, such as hydrochloric, sulfuric, phosphoric, citric, lactic or formic acid can be used. Further, other sodium salts, such as sodium citrate, sodium bicarbonate or sodium phosphate can be used in recharging the zirconium phosphate. Buffers made with the conjugate base of any of the weak acids listed can be used in place of the sodium acetate. In any embodiment, the flow rate of the zirconium phosphate recharging solution through the zirconium phosphate can be set as between any of 0.01 to 9.0 ml/min per gram of zirconium phosphate, 0.1 to 1 ml/min per gram of zirconium phosphate, 0.5 to 2.0 ml/min per gram of zirconium phosphate, 1.5 to 4.0 ml/min per gram of zirconium phosphate, and 3.0 to 7.0 ml/min per gram of zirconium phosphate. Detailed methods on recharging zirconium phosphate are disclosed in U.S. patent application Ser. No. 14/642,847, the contents of which are incorporated herein in their entirety. In any embodiment of the first or second aspects of the invention, the sodium salt in the zirconium phosphate solution can have a concentration of between 3.20 M and 4.00 M. In any embodiment of the first or second aspects of the invention, the pH of the buffer solution used in recharging the zirconium phosphate can be between any of about 4 and about 8, about 4.5 and about 6, about 6 and about 7, or about 5.5 and about 7.5. For example, a sodium/buffer solution may maintain pH value between about 3.5 and 4.8, or between about 4.0 and 4.5 during the recharging process. In any embodiment of the first or second aspects of the invention, the concentration of base in the buffer solution can be between about 0.1 M and 0.4 M. In any embodiment of the first or second aspects of the invention, the concentration of acid in the buffer solution used to recharge the zirconium phosphate can be between 0.2 M and 0.8 M. In any embodiment of the first or second aspects of the invention, the zirconium phosphate recharging solution can be maintained between 85° C. to 100° C. during recharging of the zirconium phosphate. In any embodiment of the first or second aspects of the invention, the conductivity of the recharging solution can be between any one of 5 to 700 mS/cm, 10 to 700 mS/cm, 100 to 600 mS/cm, 200 to 500 mS/cm, 250 to 490 mS/cm, 300 to 400 mS/cm, 350 to 430 mS/cm, or 390 to 410 mS/cm. In any embodiment of the first or second aspects of the invention, the time period for recharging the zirconium phosphate can be between any one of 1-240, 2-45, 5-40, 10-60, 1-10, 1-30, 25-60, 15-30, or 10-30 minutes. In any embodiment of the first or second aspects of the invention, the volume of recharging fluid can range from any one of 0.65 to 32.5 L, 1.55 to 30.5 L, 2.50 to 25.5 L, 3.5 to 30.5 L, 5.0 to 27.5 L, 6.5 to 32.5 L, or 6.5 to 12.5 L. In any embodiment of the first or second aspects of the invention, the flow rate of the recharging solution through the zirconium phosphate can be between any of 25 and 1,500 ml/min, 100 and 1,250 ml/min, 375 and 875 ml/min, 400 and 750 ml/min, 250 and 650 ml/min, 300 and 700 ml/min, 200 and 800 ml/min, or 350 and 750 ml/min.

Figure 5:
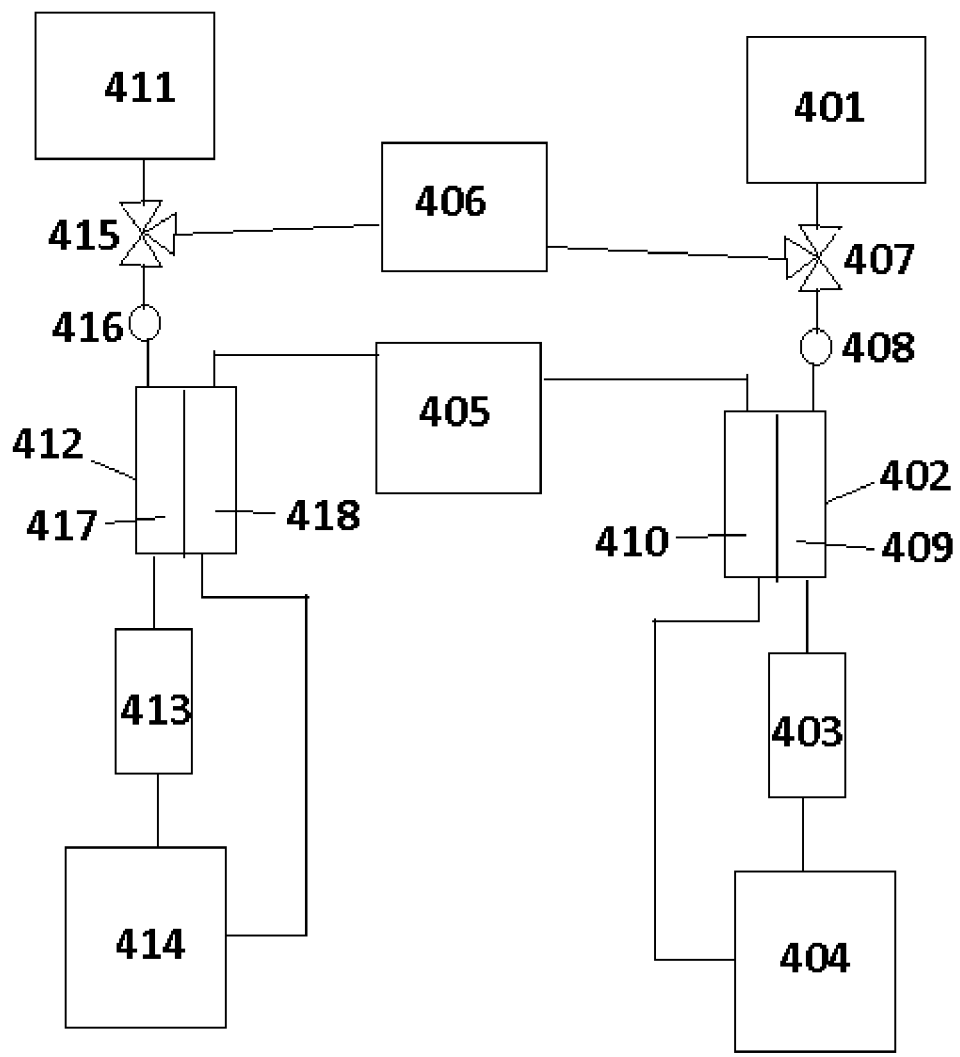
FIG. 5 shows a flow diagram of a recharger configured to recharge both zirconium oxide and zirconium phosphate with separate heaters and heat exchangers.

FIG. 5 shows a flow diagram for a recharger that is configured to recharge both a zirconium phosphate containing module and a zirconium oxide containing module. Similar to the system of FIG. 4, the system in FIG. 5 can include a zirconium oxide module 404 to be recharged. A first fluid source, such as recharging solution tank 401, can contain a zirconium oxide recharging solution, as explained. The zirconium oxide recharging solution can flow through valve 407, a first compartment 409 of heat exchanger 402, and heater 403 before entering zirconium oxide module 404. Pump 408 can provide the driving force for moving the recharging solution through the system. After passing through the zirconium oxide module 404, the used recharging solution can pass back through heat exchanger 402 in compartment 410. This will heat up the fresh zirconium oxide solution in compartment 409 of heat exchanger 402, reducing the requirements for heater 403 to heat the solution to a desired temperature. After passing through heat exchanger 402, the used recharging fluid can be directed to a drain or storage container 405. As explained, water source 406 can rinse the zirconium phosphate module 404 after recharging by switching valve 407 in order to remove any recharging solution and to cool the zirconium phosphate module 404.

The recharger can also include a zirconium phosphate module 414 for recharging. A second fluid source, such as zirconium phosphate recharging solution tank 411 can contain a zirconium phosphate recharging solution. The zirconium phosphate recharging solution can pass through valve 415, a first compartment 417 of a heat exchanger 412 and heater 413 before passing through zirconium phosphate module 414. The used zirconium phosphate recharging solution can then pass through a second compartment 418 of the heat exchanger 412, heating up the solution in compartment 417 and reducing the requirements of heater 403. After passing through compartment 418 of heat exchanger 412, the used zirconium phosphate solution can be directed to a drain or storage container 405. Pump 416 can provide the driving force necessary to move fluid through the zirconium phosphate side of the recharger. In any embodiment of the invention, the pH of the recharging solutions can be variable. The pH can be changed, such as by adding acid or base to the recharging solutions during recharging. The pH can also be controlled by allowing the recharging solution to be changed during recharging. Further, the pH can be changed by using a separately controllable acid feed as a further fluid source, wherein the separate acid feed can add acid to the recharging solutions. Changing the pH during recharging can be important if a particular pH is used for the actual recharging, and a different pH is needed for cleaning of the sorbent materials.

The zirconium phosphate module 414 can be rinsed with water from water source 406 by switching valve 415. One skilled in the art will understand that separate water sources for the zirconium phosphate and zirconium oxide modules are possible, but not necessary. Further, separate drains or storage containers are also possible but not necessary.

In any embodiment of the first or second aspects of the invention, the storage container 405 can comprise a mixer, allowing for continuous neutralization of the recharging fluids for disposal. Because the zirconium phosphate recharging fluid can be acidic, while the zirconium oxide recharging fluid is basic, combining the used fluids in a single container 405 with a mixer will cause the used recharging fluids to be neutralized and easily disposed.

Figure 6:
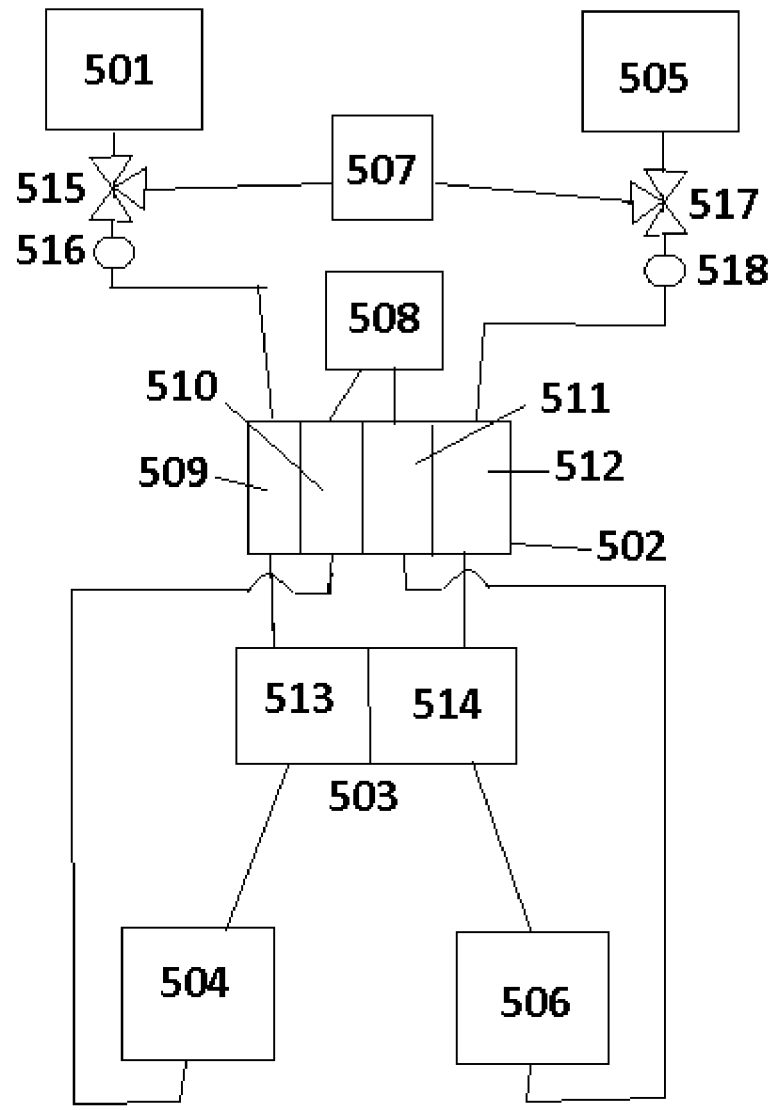
FIG. 6 shows a flow diagram of a recharger configured to recharge both zirconium oxide and zirconium phosphate with a single heater and heat exchanger.

FIG. 6 shows an additional embodiment of a recharger flow loop for recharging both zirconium oxide and zirconium phosphate. Zirconium oxide module 504 and zirconium phosphate module 506 can each be recharged with the same recharger. A first fluid source, such as zirconium oxide recharging solution tank 501, can be fluidly connected to a heat exchanger 502, a heater 503 and zirconium oxide module 504. A single heat exchanger can be used for both the zirconium oxide and zirconium phosphate recharging solutions by separating the heat exchanger 502 into additional compartments. Fresh zirconium oxide recharging solution can pass through compartment 509 of heat exchanger 502. A single heater 503 can be used for both solutions as well. Fresh zirconium oxide recharging solution can pass through compartment 513 of heater 503. Pump 516 can provide the driving force necessary to move fluid throughout the flow loop. After passing through zirconium oxide module 504, the used zirconium oxide recharging fluid can pass through compartment 510 of heat exchanger 502. This will heat the solutions in the other compartments, reducing the requirements on the heater 503. The used zirconium oxide recharging fluid can then be passed to drain or storage container 508. Similarly, pump 518 can provide the driving force to move zirconium phosphate solution from a second fluid source, such as solution tank 505, through compartment 514 of heater 503 and compartment 512 of heater 503 into zirconium phosphate module 506. Used zirconium phosphate recharging solution can pass out of zirconium phosphate module 506 and through compartment 511 of heat exchanger 502 before passing to the drain or storage container 508. A single water source 507 can provide water for rinsing both the zirconium phosphate by switching valve 517, and the zirconium oxide by switching valve 515.

In any embodiment of the first or second aspects of the invention, different temperatures can be desired for each of the zirconium phosphate recharging solution and the zirconium oxide recharging solution. This can be achieved even with the system illustrated in FIG. 6 that uses a single heater and heat exchanger. For example, the heat exchanger can be eliminated for the zirconium oxide recharging solution if the desired zirconium oxide recharging solution temperature is lower than the desired zirconium phosphate recharging solution temperature. Further, the flow rates of each of the solutions can be controlled independently, allowing differing conditions for each of the zirconium phosphate and zirconium oxide modules.

Figure 7:
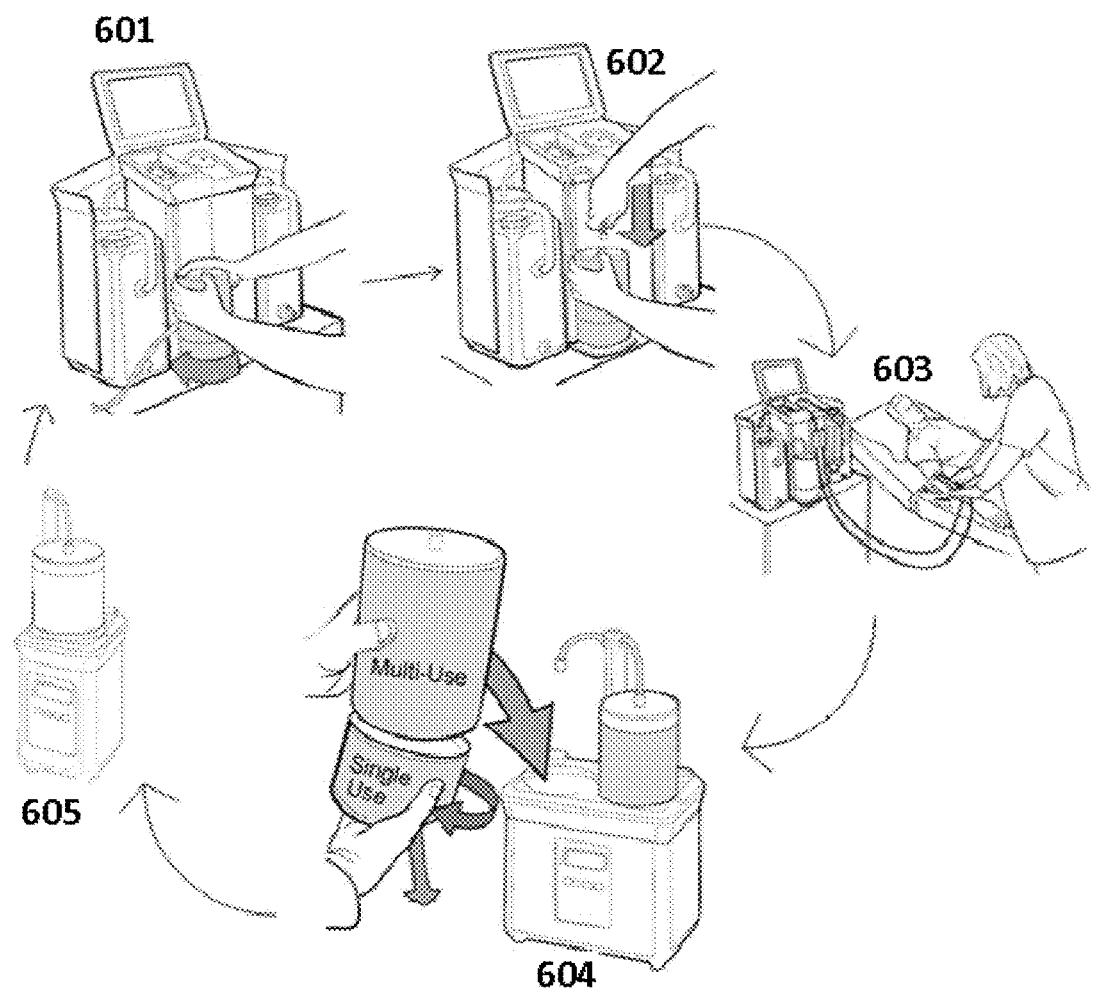
FIG. 7 shows the steps of preparing a dialysis session, performing dialysis, and recharging a multi-use module containing a rechargeable sorbent material.

A flow chart showing the steps for utilizing the method and apparatus of the invention is shown in FIG. 7. In step 601, one or more multi-use and single use modules can be connected together to form a sorbent cartridge. Although shown as a two-module system in FIG. 7, the sorbent cartridge can comprise 3 or more modules as explained. In any embodiment of the first or second aspects of the invention, more than one module can be a multi-use module, as explained. In step 602 the user can ensure that the zirconium phosphate and/or zirconium oxide in the multi-use module or modules has been recharged and that the single use module has not been previously used. In any embodiment of the first or second aspects of the invention, the recharging process can be tracked by the use of bar codes or RFID tags to keep track of whether the multi-use module has been recharged. After ensuring all modules are ready to be used, the sorbent cartridge can be connected to the dialysis system. In step 603, the patient can be connected to an extracorporeal circuit attached to the dialysis machine to circulate the patient's blood, and a dialysis session can be carried out and the patient treated. After dialysis, the sorbent cartridge can be disconnected from the dialysis system in step 604. The multi-use module or modules can be separated from the single use module in step 604 as explained herein. The single use module can be discarded, or sent to a recycling, replenishing or recharging facility. The multi-use module or modules can be connected to a recharger and recharged in step 605. In any embodiment of the first or second aspects of the invention, a single recharger can be used to recharge multiple multi-use modules, including multi-use modules containing differing sorbent materials, as explained. The multi-use module or modules, after recharging, can be connected to a new single use module and reused starting again at step 601.

In any embodiment of the first or second aspects of the invention, a multi-use module, containing either zirconium phosphate or zirconium oxide, can be stored for a period of time before reuse. In order maintain the zirconium phosphate with the correct ratio of hydrogen to sodium ions within the module, the multi-use module containing zirconium phosphate can be filled with a buffer solution for the storage. In any embodiment of the first or second aspects of the invention, the buffer solution used during storage can have a pH of between about 3 and about 8. The zirconium oxide module can be stored with a water solution.

The fluid connections connecting the multi-use modules to each other and the single use module can be any type of connections known in the art. The connections can be permanently placed on each of the modules, or can be separate components that can be attached to each of the modules for connection.

Figure 8A:
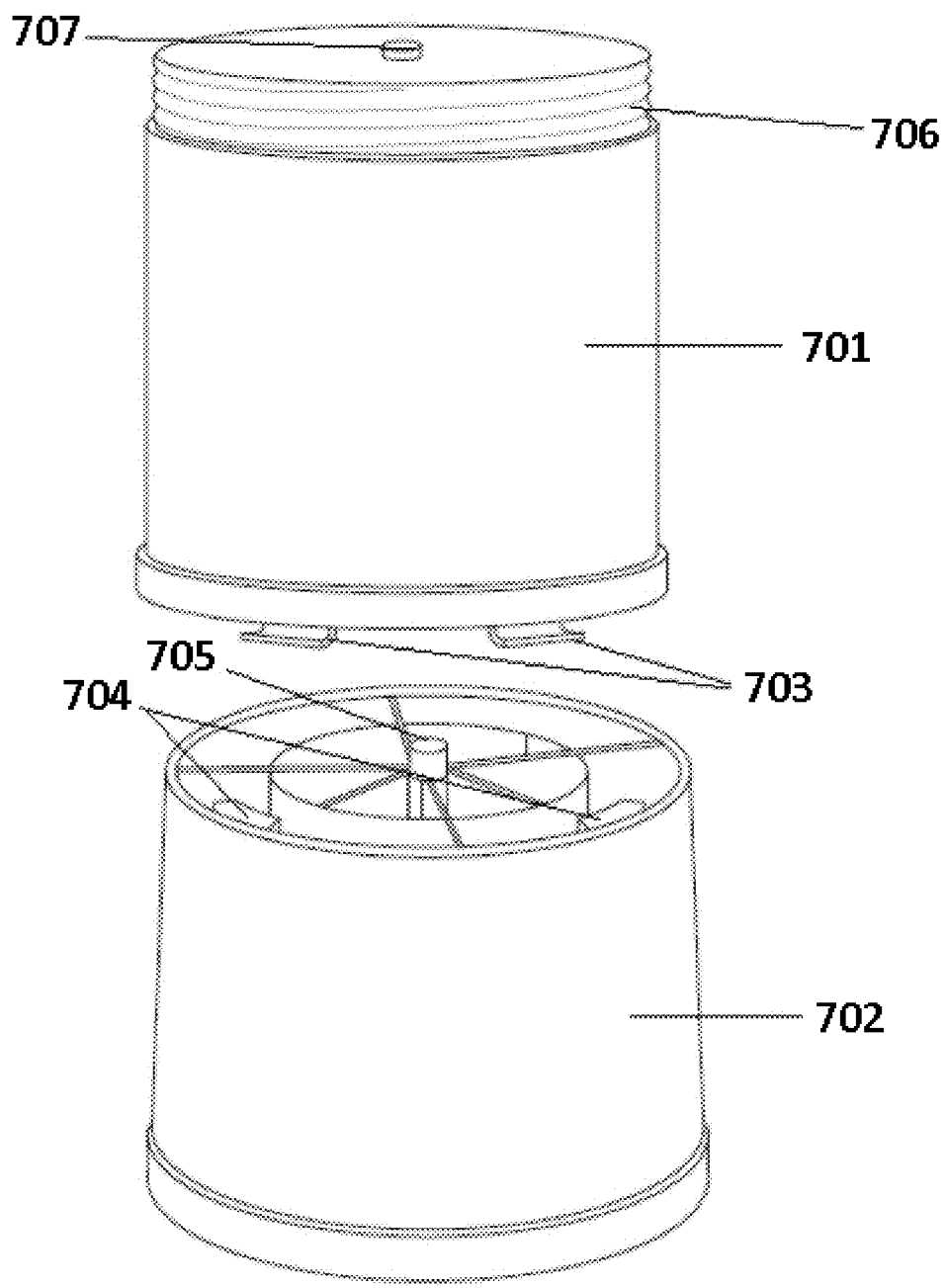
FIG. 8a shows separate sorbent modules that can be connected together.

In any embodiment of the first or second aspects of the invention, engagement members can be disposed on both the multi-use and single use modules, as shown in FIG. 8a. The engagement members can provide complementary joining or attachment of the single use modules and multi-use modules into a particular configuration. The engagement members can allow for compartments to cooperatively engage. In any embodiment of the first or second aspects of the invention, these engagement members may be clasps, latches, or any known releasable fastening means. In general, the engagement members can interact to form a cooperative engagement and prevent inadvertent detachment of the multi use modules and single use modules from each other. For example, a multi-use module 701 can have engagement members 703 disposed around the bottom circumference of the module 701. A single use module or a second multi-use module 702 can have receiving grooves 704 for the engagement members 703. When the engagement members 703 from the multi use module 701 are inserted under the receiving grooves 704 on the single use module 702, the engagement members 703 can snap into place, locking the modules together. One skilled in the art will understand that the engagement members may be disposed on the top portion of the single use module, and the receiving grooves disposed on the bottom portion of the multi-use module. During use, fluid can enter through a fluid inlet (not shown) in the bottom of the single use module 702. After traveling through the single use module, the fluid can pass through fluid outlet 705 at the top of the single use module 702. When connected to the multi-use module 701, this fluid outlet 705 can fit into a fluid inlet (not shown) at the bottom of the multi-use module 701. After traveling through the multi-use module 701 fluid can exit through fluid outlet 707. The fluid outlet 707 can connect to the dialysis circuit as explained herein. Optional threaded portion 706 of the multi-use module 701 can connect as a screw type connection to the dialysis circuit or recharger as explained herein. As explained, a sorbent cartridge can comprise more than two modules, including multiple multi-use modules each comprising differing sorbent materials.

Figure 8B:
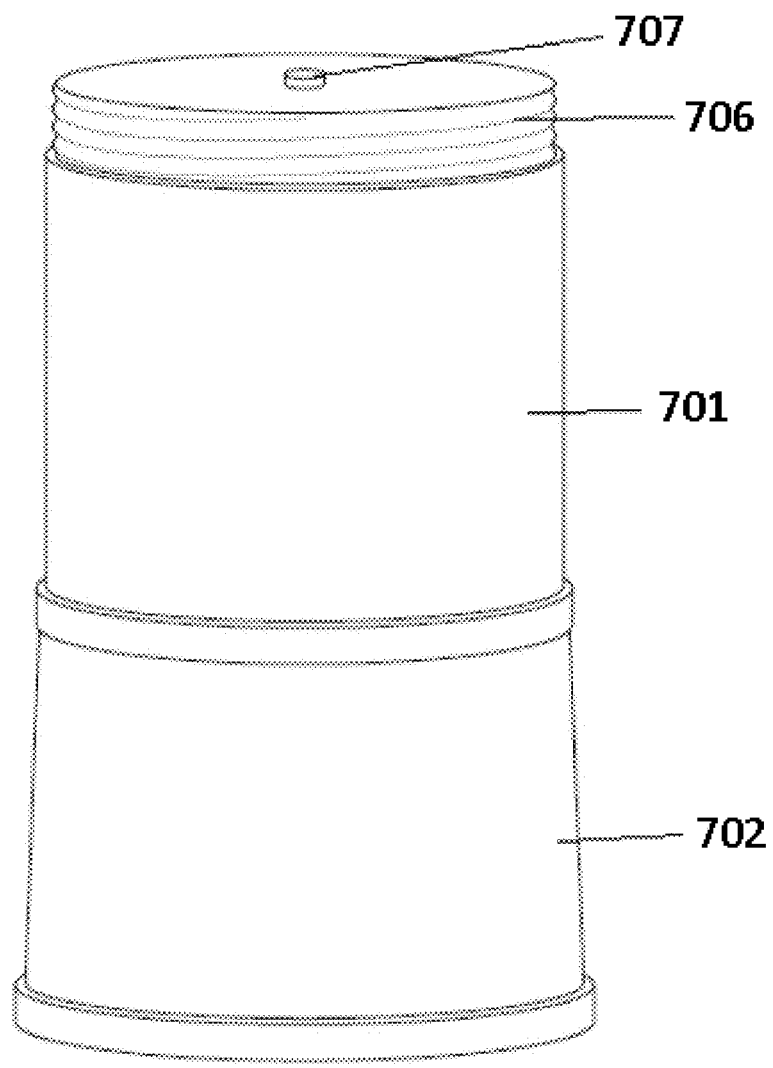
FIG. 8b shows two sorbent modules after the modules have been connected.

FIG. 8b shows a single use module 702 and multi-use module 701 when connected together. Fluid can travel through the single use module 702, and into the multi use module 701. Fluid can exit the combined modules through fluid outlet 707 for connection to a dialysis machine or additional modules. In any embodiment of the first or second aspects of the invention, an o-ring or gasket can be disposed on the circumference of one or both of the modules to prevent leakage.

In any embodiment of the first or second aspects of the invention, the fluid connection between any two modules can be a screw on variety. A first module can have a threaded male portion of a screw connector disposed on the top of the module. A second module can have a female receiving portion of a screw connector with internal threading disposed on the bottom of the module. In setting up the dialysis session, the user can place the first module connector inside the second module connector and twist the modules in opposite directions to secure the modules together. This process can be repeated for each module in the modular sorbent cartridge. The interior of each portion of the screw type connection can be hollow, allowing fluid to flow from the first module to the second module. One skilled in the art will understand that the male and female portions of the connector can be reversed, so that the male portion is on the second module and the female portion is on the first module.

In any embodiment of the first or second aspects of the invention, the screw connectors do not have to be hollow. Instead, grooves can be made on the exterior of the male portion of the screw connector. These grooves can be large enough to allow fluid to flow through the grooves and into the female receiving portion on the multi-use module. The grooves, once the modules are connected together, will be entirely inside the female portion, allowing fluid to flow between the modules without leakage.

In any embodiment of the first or second aspects of the invention, the connection between any two modules can be a length of tubing. The tubing can attach to an attachment point at the outlet of a first module, and to an attachment point at the inlet of a second module. The tubing provides for a fluid pathway from the single use module to the multi-use module.

Alternatively, in any embodiment of the first or second aspects of the invention, the top of a first use module and the bottom of a second module can both have a number of fluid channels or passageways built thereon. In any embodiment of the first or second aspects of the invention, these passageways can simply be holes drilled in the top or bottom surface of the respective modules. In any embodiment of the first or second aspects of the invention, the channels can extend into the interior of the respective modules. The outer portions of the modules can connect together in such a way as to prevent leakage of fluid passing between the modules. The modules can connect with screw type fittings or any other method known in the art. In any embodiment of the first or second aspects of the invention, gaskets or o-rings can be placed on the outer edges of the modules to ensure proper sealing when connected. In use, the fluid from the first module can pass through the passages or channels in the top of the first module, and then through the channels or passages in the second module to enter the interior of the second module.

Figure 9:
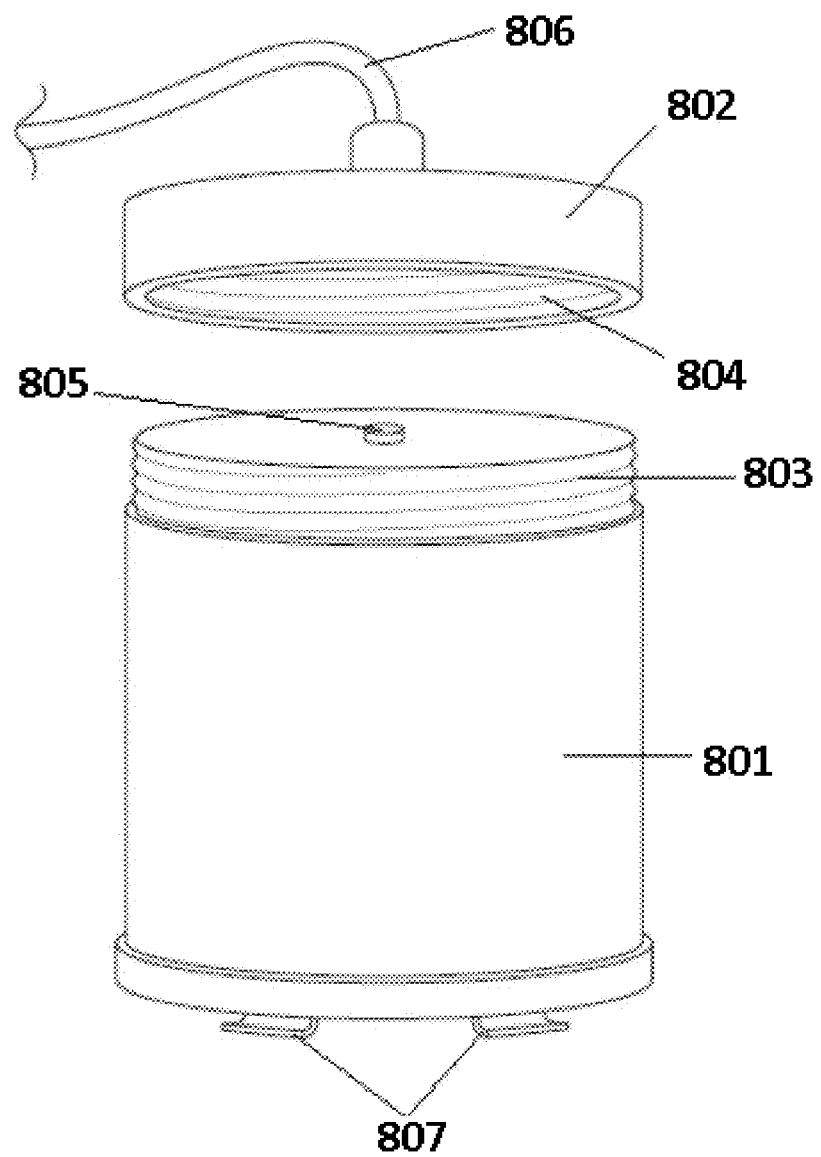
FIG. 9 shows a connection between a multi-use module and a recharger.

One embodiment of a connection for connection of a multi-use module to a recharger of the first or second aspects of the invention is shown in FIG. 9. Multi-use module 801 can have a threaded portion 803 at the top of the module 801. The recharger connector 802 can have a complimentary threaded portion 804 on the interior of the recharger connector 802. The recharger connector 802 can fit over the top of multi-use module 801 and when turned screw onto the multi-use module 801 to form the connection. During recharging, fluid can be passed through hose 806, and into the multi-use module 801 through inlet 805. Engagement members 807 can be used to facilitate connection to the basin of the recharger as explained herein. In any embodiment of the first or second aspects of the invention, the bottom portion of the multi-use module 801 can also have a threaded portion, and the module 801 can connect to the basin of the recharger in the same fashion as the top. In systems where using more than one multi-use module, such as a system with a multi-use module containing zirconium oxide and a multi-use module containing zirconium phosphate, the connections to the recharger can be different. For example, the recharger connector for connecting to a zirconium phosphate module can be of a different size than the recharger connector for connecting to a zirconium oxide module. This ensures that a user cannot connect a module containing zirconium oxide to a recharger connector that will pass a zirconium phosphate recharging solution through the module.

Figure 10:
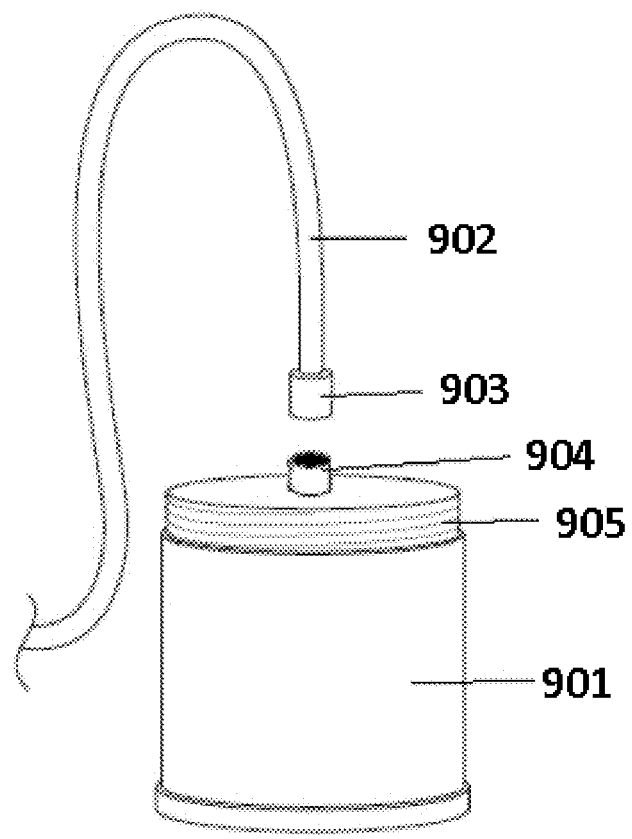
FIG. 10 shows a connection between a sorbent module and a dialysis system.

One embodiment of a connection between the module and the dialysis system of the first or second aspects of the invention is shown in FIG. 10. The sorbent module 901 can connect to a hose or tubing 902 through connector 903. The connector 903 can fit over fluid outlet 904 at the top of the sorbent module 901. Fluid from the sorbent module 901 can exit through the fluid outlet 904 and enter the tubing 902 through connector 903. In any embodiment of the first or second aspects of the invention, connector 903 can be a clamp, such that the connector 903 tightens around the fluid outlet 904 when turned. In any embodiment of the first or second aspects of the invention, the tubing 902 can be secured to the fluid outlet 902 with the use of external clamps, wires or other means. In any embodiment of the first or second aspects of the invention, fluid outlet 904 can have a threaded exterior, and connector 903 can have a complimentarily threaded interior, such that the fluid outlet 904 can be connected to connector 903 in a screw-type fashion. In any embodiment of the first or second aspects of the invention, the connection to the dialysis system can be similar to the connection to the recharger shown in FIG. 10, utilizing threaded portion 905 of the sorbent module 901.

In any embodiment of the first or second aspects of the invention, the connectors on the top and bottom of each of the modules can be separate from the modules themselves. That is, the connectors can attach to the modules and need not be formed integrally with the modules. The connectors can be fastened to the module in any fashion known in the art, such as with screws or bolts. The connectors can be removed and different connectors added as necessary, such as with connector 211 in FIG. 3. For example, the fluid connectors that connect the multi-use module to the single use module can be different from the fluid connector that connects the multi-use module to the recharging apparatus as explained herein. The user need only remove the connector from the multi-use module after a dialysis session and then replace the connector with the proper connector to connect to the recharging apparatus. One skilled in the art will understand that any type of fluid connection can be used without detracting from the scope of this invention. Any type of fluid connections described for connecting two modules, a module to the dialysis system, or a module to the recharging apparatus, can be used for any of the fluid connections of the invention.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A method, comprising the steps of:
   recharging zirconium oxide by passing a basic aqueous solution through the zirconium oxide; wherein the zirconium oxide is present in at least one sorbent module for use in sorbent dialysis;
   wherein the basic aqueous solution is passed through the zirconium oxide from a first fluid source of a recharger through a fluid flow path fluidly connecting the first fluid source to the at least one sorbent module containing zirconium oxide; wherein the first fluid source contains the basic aqueous solution.

2. The method of claim 1, wherein the basic aqueous solution comprises any one or more bases selected from the group consisting of sodium hydroxide, lithium hydroxide, potassium hydroxide, and combinations thereof.

3. The method of claim 2, wherein a concentration of the base is between any of 0.1 M and 5.0 M, 0.1 M and 0.5 M, 0.3 M and 0.7 M, 0.6 M and 1.0 M, 0.5 M and 1.5 M, 1.0 M and 2.5 M, 2.0 M and 3.5 M, or 3.0 M and 5.0 M.

4. The method of claim 1, further comprising maintaining a temperature of the basic aqueous solution at between any of about 20° C. and about 105° C., 25° C. to about 80° C., 35° C. to about 75° C., 40° C. to about 70° C., 50° C. to about 60° C., 25° C. to about 50° C., 50° C. to about 75° C., or 60° C. to about 105° C.

5. The method of claim 1 wherein a flow rate of the basic aqueous solution passed through the zirconium oxide is between any of 10 ml/min to 750 ml/min, 10 ml/min to 100 ml/min, 50 ml/min to 250 ml/min, 200 ml/min to 250 ml/min, 250 ml/min to 400 ml/min, 300 ml/min to 550 ml/min and 500 ml/min to 750 ml/min.

6. The method of claim 5, further comprising rinsing the zirconium oxide with water after passing the basic aqueous solution through the zirconium oxide.

7. The method of claim 6 further comprising draining the zirconium oxide after rinsing the zirconium oxide by blowing air through the zirconium oxide.

8. The method of claim 1, wherein the at least one sorbent module is fluidly connectable to one or more additional sorbent modules containing sorbent materials to form a sorbent cartridge.

9. A recharger, comprising:
a first fluid source fluidly connectable to at least a first sorbent module for use in sorbent dialysis; wherein the first sorbent module is configured to contain zirconium oxide; wherein the first fluid source is configured to contain a first recharging solution capable of recharging the zirconium oxide in the first sorbent module; and
a fluid flow path fluidly connected to the first fluid source and fluidly connectable to an inlet of the first sorbent module;
wherein the first recharging solution is a basic aqueous solution.

10. The recharger of claim 9, further comprising a pump to pump fluid flow through the fluid flow path.

11. The recharger of claim 9, wherein the recharger is fluidly connectable to at least a second sorbent module.

12. The recharger of claim 11, wherein the first and second sorbent modules both contain zirconium oxide.

13. The recharger of claim 12, wherein the fluid flow path is fluidly connected to the first fluid source and is fluidly connectable to each of the first and second sorbent modules.

14. The recharger of claim 11, wherein the first sorbent module contains a sorbent material that is different from a sorbent material contained in the second sorbent module.

15. The recharger of claim 14, wherein the recharger comprises a second fluid source configured to contain a second recharging solution that is different from the first recharging solution, and a second fluid flow path fluidly connected to the second fluid source and fluidly connectable to the second sorbent module.

16. The recharger of claim 15 wherein the second sorbent module is configured to contain zirconium phosphate; and wherein the second recharging solution is a solution of an acid, a buffer, a sodium salt or combinations thereof.

17. The recharger of claim 15, wherein fluid flow through the first fluid flow path is controlled by a first pump; and wherein fluid flow through the second fluid flow path is controlled by a second pump.

18. The recharger of claim 9, further comprising a water source, wherein the water source is fluidly connectable to the fluid flow path.

19. The recharger of claim 18, wherein the fluid flow path further comprises a valve, wherein the valve controls movement of fluid from either the first fluid source or the water source into the fluid flow path.

20. The recharger of claim 9, further comprising a heater in the fluid flow path; wherein the heater heats the first recharging fluid before the first recharging fluid enters the first sorbent module.

21. The recharger of claim 20, further comprising a heat exchanger, wherein the heat exchanger comprises at least a first compartment and a second compartment, wherein fluid in the fluid flow path enters the first compartment before the heater heats the fluid and before entering the first sorbent module, and wherein the fluid flow path fluidly connects an outlet of the first sorbent module to the second compartment of the heat exchanger.

22. The recharger of claim 15, further comprising a first heater and a second heater, wherein the first heater heats the first recharging solution before the first recharging solution enters the first sorbent module, and wherein the second heater heats the second recharging solution before the second recharging solution enters the second sorbent module.

23. The recharger of claim 15, further comprising a heater, wherein the heater heats the first recharging solution before the first recharging solution enters the first sorbent module, and wherein the heater heats the second recharging solution before the second recharging solution enters the second sorbent module.

24. The recharger of claim 11, wherein the recharger is fluidly connectable to at least two sorbent modules each configured to contain zirconium oxide.

25. The recharger of claim 14, wherein the recharger is fluidly connectable to one or more sorbent modules configured to contain zirconium oxide and one or more sorbent modules configured to contain zirconium phosphate.

26. The method of claim 1, wherein the at least one sorbent module is a multi-use sorbent module.

27. The recharger of claim 9, wherein the first sorbent module is a multi-use sorbent module.

* * * * *